United States Patent
Poole et al.

(10) Patent No.: US 11,154,433 B2
(45) Date of Patent: Oct. 26, 2021

(54) DISPOSABLE ARTICLE WITH REINFORCED HANDLE

(71) Applicant: Kimberly-Clark Worldwide, Inc., Neenah, WI (US)

(72) Inventors: Cole W. Poole, Appleton, WI (US); Chris P. Olson, Neenah, WI (US); Julie A. Paveletzke, Appleton, WI (US); John D. Amundson, Greenville, WI (US); Susan M. Trefethren, Appleton, WI (US); Catherine M. Hancock-Cooke, Neenah, WI (US); Adam Suttner, Appleton, WI (US); Russell J. Brumm, Menasha, WI (US); Bradley A. Colvin, Appleton, WI (US); Tim G. Dollevoet, Appleton, WI (US); Christopher M. Pieper, Hortonville, WI (US); Andrew M. Long, Appleton, WI (US); Sandra K. Walker, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 1089 days.

(21) Appl. No.: 15/517,994

(22) PCT Filed: Oct. 28, 2015

(86) PCT No.: PCT/US2015/057714
§ 371 (c)(1),
(2) Date: Apr. 10, 2017

(87) PCT Pub. No.: WO2016/069692
PCT Pub. Date: May 6, 2016

(65) Prior Publication Data
US 2017/0246051 A1  Aug. 31, 2017

Related U.S. Application Data

(60) Provisional application No. 62/073,133, filed on Oct. 31, 2014.

(51) Int. Cl.
*A61F 13/496* (2006.01)
*A61F 13/49* (2006.01)
(Continued)

(52) U.S. Cl.
CPC .... *A61F 13/4963* (2013.01); *A61F 13/49001* (2013.01); *A61F 13/49011* (2013.01);
(Continued)

(58) Field of Classification Search
CPC ........ A61F 2013/49098; A61F 13/4963; A61F 13/5633; A61F 13/565; A61F 13/84;
(Continued)

(56) References Cited

U.S. PATENT DOCUMENTS 507,485 A    10/1893  Carr et al.
2,782,420 A   2/1957  Barager
(Continued)

FOREIGN PATENT DOCUMENTS

CN    1348347 A    5/2002
CN  101237841 A    8/2008
(Continued)

*Primary Examiner* — Tatyana Zalukaeva
*Assistant Examiner* — Jessica R Arble
(74) *Attorney, Agent, or Firm* — Kimberly-Clark Worldwide, Inc.

(57) ABSTRACT

A pant-like absorbent articles having handles on side panels of the article for ease of removal and donning of the absorbent garment is disclosed. The article includes a front waist region, a back waist region, and a chassis extending longitudinally between and interconnecting the front and back waist regions attached by at least one side panel. Formed within the side panel is at least one handle. The (Continued)

handle includes an aperture formed through the side panel. The handle further includes a reinforcing material operatively joined to the at least one side panel adjacent distal side edges of the aperture.

31 Claims, 5 Drawing Sheets

(51) Int. Cl.
*A61F 13/56* (2006.01)
*A61F 13/84* (2006.01)

(52) U.S. Cl.
CPC ...... *A61F 13/49014* (2013.01); *A61F 13/565* (2013.01); *A61F 13/5633* (2013.01); *A61F 13/84* (2013.01)

(58) Field of Classification Search
CPC .......... A61F 13/49001; A61F 13/49014; A61F 13/49011
See application file for complete search history.

(56) References Cited

U.S. PATENT DOCUMENTS

| | | | |
|---|---|---|---|
| 3,685,818 A | 8/1972 | Burger et al. |
| 3,773,214 A | 11/1973 | Lemon |
| 3,875,621 A | 4/1975 | Rami |
| 3,951,149 A | 4/1976 | Ness et al. |
| 3,994,486 A | 11/1976 | Nystrand |
| 4,100,324 A | 7/1978 | Anderson et al. |
| 4,610,680 A | 9/1986 | Lafleur |
| 4,619,649 A | 10/1986 | Roberts |
| 4,663,220 A | 5/1987 | Wisneski et al. |
| 4,747,846 A | 5/1988 | Boland et al. |
| 4,795,510 A | 1/1989 | Wittrock et al. |
| 4,850,988 A | 7/1989 | Aledo et al. |
| 4,909,804 A | 3/1990 | Douglas, Sr. |
| 4,940,464 A | 7/1990 | Van Gompel et al. |
| 5,046,272 A | 9/1991 | Vogt et al. |
| 5,053,028 A | 10/1991 | Zoia et al. |
| 5,094,658 A | 3/1992 | Smithe et al. |
| 5,104,116 A | 4/1992 | Pohjola |
| 5,163,932 A | 11/1992 | Nomura et al. |
| 5,224,405 A | 7/1993 | Pohjola |
| 5,226,992 A | 7/1993 | Morman |
| 5,284,703 A | 2/1994 | Everhart et al. |
| 5,350,624 A | 9/1994 | Georger et al. |
| 5,385,775 A | 1/1995 | Wright |
| 5,486,166 A | 1/1996 | Bishop et al. |
| 5,490,846 A | 2/1996 | Ellis et al. |
| 5,531,732 A | 7/1996 | Wood |
| 5,624,420 A | 4/1997 | Bridges et al. |
| 5,705,013 A | 1/1998 | Nease et al. |
| 5,820,973 A | 10/1998 | Dodge, II et al. |
| 5,827,260 A | 10/1998 | Suzuki et al. |
| 6,004,306 A | 12/1999 | Robles et al. |
| 6,057,024 A | 5/2000 | Mleziva et al. |
| 6,213,991 B1 | 4/2001 | Kling et al. |
| 6,302,871 B1 | 10/2001 | Nakao et al. |
| 6,447,628 B1 | 9/2002 | Couillard et al. |
| 6,481,362 B2 | 11/2002 | Hietpas et al. |
| 6,525,238 B2 | 2/2003 | Corrales |
| 6,596,113 B2 | 7/2003 | Csida et al. |
| 6,746,433 B1 | 6/2004 | Shimoe et al. |
| 6,854,624 B2 | 2/2005 | Vogt et al. |
| 6,875,710 B2 | 4/2005 | Eaton et al. |
| 6,916,750 B2 | 7/2005 | Thomas et al. |
| 6,968,992 B2 | 11/2005 | Schuster |
| 6,969,441 B2 | 11/2005 | Welch et al. |
| 7,156,834 B2 | 1/2007 | Kawata et al. |
| 7,175,584 B2 | 2/2007 | Maxton et al. |
| 7,217,260 B2 * | 5/2007 | Molander ......... A61F 13/49015 604/385.24 |
| 7,255,688 B2 | 8/2007 | Sasaki et al. |
| 7,322,925 B2 | 1/2008 | Couillard et al. |
| 7,335,150 B2 | 2/2008 | Coenen et al. |
| 7,387,148 B2 | 6/2008 | Vogt et al. |
| 7,452,320 B2 | 11/2008 | Csida et al. |
| 7,534,481 B2 | 5/2009 | Seth et al. |
| 7,744,577 B2 | 6/2010 | Otsubo et al. |
| 7,803,244 B2 | 9/2010 | Siqueira et al. |
| 7,806,880 B2 | 10/2010 | Roe et al. |
| 7,887,522 B2 | 2/2011 | Roe et al. |
| 7,985,210 B2 | 7/2011 | Ashton et al. |
| 8,034,040 B2 | 10/2011 | Sasaki et al. |
| 8,066,687 B2 | 11/2011 | Ashton et al. |
| 8,235,962 B2 | 8/2012 | Popp et al. |
| 8,262,636 B2 | 9/2012 | Sperl |
| 8,337,479 B2 | 12/2012 | Nilsson et al. |
| 8,361,913 B2 | 1/2013 | Siqueira et al. |
| 8,556,790 B2 | 10/2013 | Fujita |
| 8,821,360 B2 | 9/2014 | Umebayashi |
| 8,936,586 B2 | 1/2015 | Roe |
| 8,936,589 B2 | 1/2015 | Shturman |
| 8,939,876 B2 | 1/2015 | Schneider et al. |
| 2002/0111596 A1 | 8/2002 | Fletcher et al. |
| 2002/0138059 A1 | 9/2002 | Van Gompel et al. |
| 2003/0087059 A1 | 5/2003 | Jackson et al. |
| 2004/0186451 A1 | 9/2004 | Bishop et al. |
| 2005/0130821 A1 | 6/2005 | Reising et al. |
| 2005/0175269 A1 | 8/2005 | Ashton et al. |
| 2006/0025737 A1 | 2/2006 | Song et al. |
| 2006/0155255 A1 | 7/2006 | McKiernan et al. |
| 2006/0167434 A1 | 7/2006 | Ashton et al. |
| 2007/0029035 A1 | 2/2007 | Desai et al. |
| 2007/0083177 A1 | 4/2007 | Takino et al. |
| 2007/0233033 A1 | 10/2007 | Ichikawa et al. |
| 2008/0045918 A1 | 2/2008 | Driskell |
| 2008/0108963 A1 | 5/2008 | Ashton et al. |
| 2008/0114322 A1 | 5/2008 | Schmoker et al. |
| 2008/0311338 A1 | 12/2008 | Petersen et al. |
| 2009/0149827 A1 | 6/2009 | Mlinar et al. |
| 2010/0004616 A1 | 1/2010 | Nakamura et al. |
| 2011/0313380 A1 | 12/2011 | Ashton et al. |
| 2012/0101463 A1 | 4/2012 | Sperl |
| 2012/0101468 A1 | 4/2012 | Sperl |
| 2012/0157953 A1 | 6/2012 | Ashton et al. |
| 2012/0208688 A1 | 8/2012 | Sakaguchi et al. |
| 2012/0209230 A1 * | 8/2012 | Mansfield ......... A61F 13/15203 604/361 |
| 2012/0225764 A1 | 9/2012 | Ogasawara |
| 2013/0231629 A1 | 9/2013 | Paveletzke et al. |
| 2014/0228192 A1 | 8/2014 | Schuster |
| 2014/0257227 A1 * | 9/2014 | Roe ..................... A61F 13/4906 604/385.14 |
| 2015/0144251 A1 | 5/2015 | Schoultz et al. |

FOREIGN PATENT DOCUMENTS

| | | |
|---|---|---|
| CN | 101460130 A | 6/2009 |
| EP | 0 217 032 A2 | 4/1987 |
| JP | 11-043801 A | 2/1999 |
| JP | 11-104180 A | 4/1999 |
| JP | 2008-212485 A | 9/2008 |
| JP | 2012-075458 A | 4/2012 |
| WO | WO 1989/007897 A1 | 9/1989 |
| WO | WO 1998/013002 A1 | 4/1998 |
| WO | 0187562 A2 | 11/2001 |
| WO | WO 2001/088245 A2 | 11/2001 |

* cited by examiner

DISPOSABLE ARTICLE WITH REINFORCED HANDLE

RELATED APPLICATIONS

The present application claims priority to U.S. Provisional Application No. 62/073,133 entitled DISPOSABLE ARTICLE WITH REINFORCED HANDLE; and filed Oct. 31, 2014; U.S. Provisional Application No. 62/073,172 entitled DISPOSABLE ARTICLE WITH HANDLE HAVING OPTIMIZED STRENGTH PROPERTIES and filed Oct. 31, 2014; and U.S. Provisional Application No. 62/073,296 entitled DISPOSABLE ARTICLE WITH HANDLE WITH OPTIMIZED SHAPE AND LOCATION and filed Oct. 31, 2014, the contents of which are hereby incorporated by reference in a manner consistent with the present application.

BACKGROUND

Many absorbent articles intended for personal wear such as diapers, training pants, feminine hygiene products, adult incontinence products, bandages, medical garments and the like are designed to be sufficiently absorbent to pull moisture from liquid body exudates including urine, menses, blood, etc. away from the wearer to reduce skin irritation caused by prolonged exposure to wetness. Diapers, as an example, are typically placed and secured on a wearer using a set of primary fastening tabs, such as adhesive tabs or mechanical (e.g., hook or loop) fastening system tabs and left in place to absorb insults as well as to contain fecal waste.

Training pants, unlike diapers, typically come pre-assembled in a wear configuration to more closely resemble conventional underpants. In particular, front and back waist regions of such training pants are typically attached at a seam either permanently or refastenably (such as by a primary fastening system) to define a wear configuration of the pants having a waist opening and leg openings. Such design enables pull-on prefastened garments to allow for self-application and removal.

Unfortunately, current pull-on prefastened garments have not been optimized for child application. While children of potty training age desire to complete tasks independently, they typically lack the dexterity and cognitive ability to successfully don current pull-on prefastened garments on their own. As a result, most of the time the caregiver will either don the product completely, assist the child during the donning process, or readjust the pant after the child tries unsuccessfully on his or her own. In addition to being difficult to grab, there are no cues that direct the child as to where to hold the garment. Left on their own, children typically try to pull on the product by holding the front or the back of the garment. When the garment is pulled on by holding the front, it usually gets stuck beneath the buttocks. Holding the product at the back is difficult for the child and results in the product not coming up completely at the front. In both instances, readjustment is required by the caregiver.

Thus, there is a need to provide an optimized handle for use with absorbent articles that have the necessary strength and design that enables a toddler to successfully pull-on the garment.

SUMMARY

The present disclosure is directed to a pant-like absorbent articles having handles on side panels of the article for ease of removal and donning of the absorbent garment. In one embodiment, the article includes a liquid permeable inner surface for facing the wearer, an outer surface for facing away from the wearer, an absorbent body disposed therebetween. The article further includes a front waist region, a back waist region, and a crotch region extending longitudinally between and interconnecting the front and back waist regions. At least one side panel is attached to the front waist region and the back waist region to define a wear configuration of the absorbent article having a waist opening and a leg opening spaced from the waist opening, wherein the at least one side panel extends from the waist opening to the leg opening. Formed within the side panel is at least one handle. The handle includes an aperture formed through the side panel. The handle further includes a reinforcing material operatively joined to the at least one side panel adjacent distal side edges of the aperture at the longitudinal midpoint of the aperture.

In another embodiment, the article includes a liquid permeable inner surface for facing the wearer, an outer surface for facing away from the wearer, an absorbent body disposed therebetween. The article further includes a front waist region, a back waist region, and a crotch region extending longitudinally between and interconnecting the front and back waist regions. A front side panel is attached to the front waist region and a back side panel is attached to the back waist region. The front and back side panels are releasably attachable at a refastenable seam to define a wear configuration of the absorbent article having a waist opening and a leg opening spaced from the waist opening, wherein the front and back side panels each extend from the waist opening to the leg opening. Formed within the side panel is at least one handle. The handle further includes a reinforcing material operatively joined to the back side panel adjacent distal side edges of the aperture at the longitudinal midpoint of the aperture.

DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

DEFINITIONS

It is to be understood by one of ordinary skill in the art that the present discussion is a description of exemplary aspects of the present disclosure only, and is not intended as limiting the broader aspects of the present disclosure.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Cross direction" refers to the width of a fabric in a direction generally perpendicular to the direction in which it is produced, as opposed to "machine direction" that refers to the length of a fabric in the direction in which it is produced.

Figure 1:
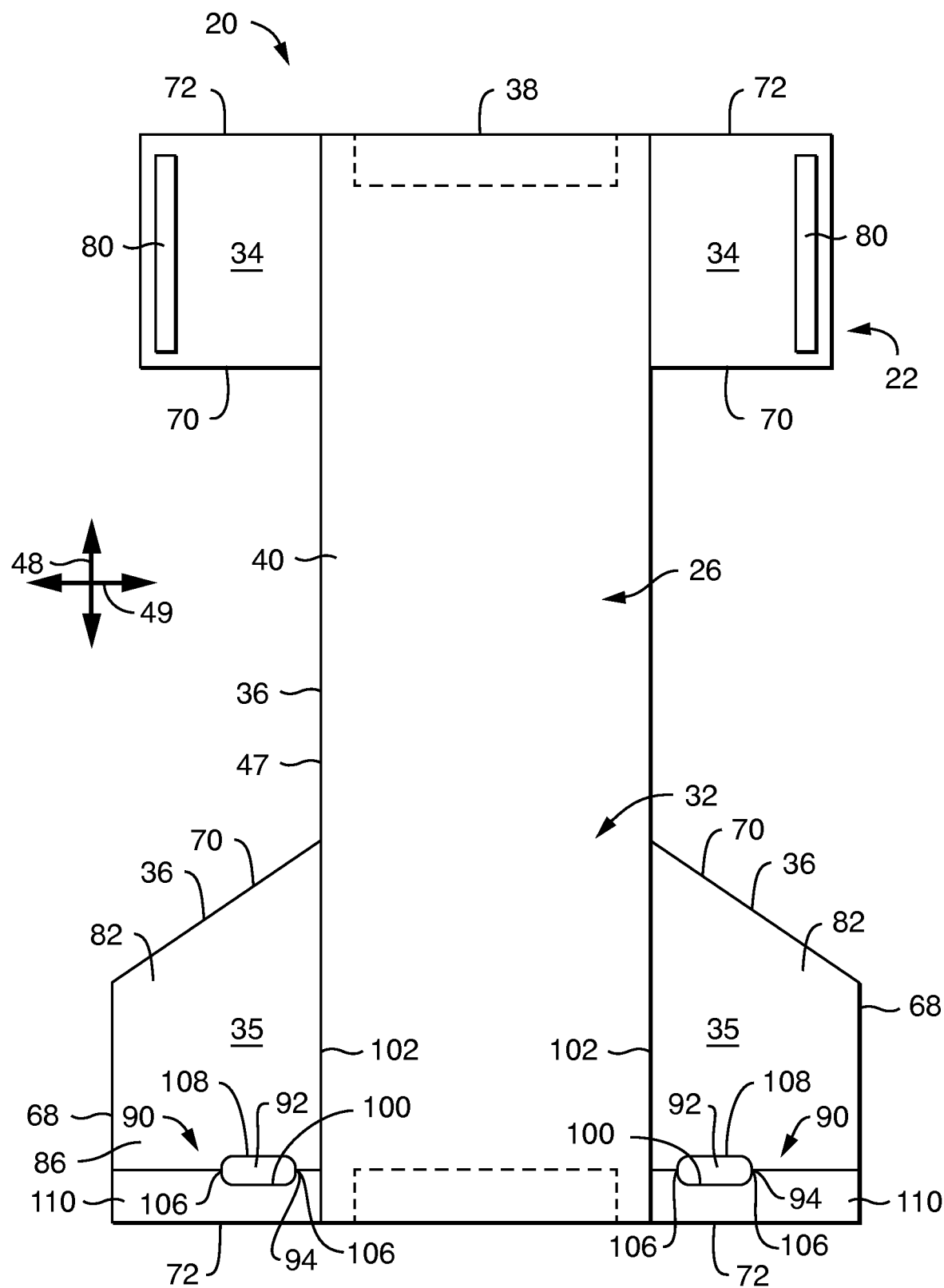
FIG. 1 is a bottom plan view of one aspect of a personal wear article in the form of a pair of training pants having a handle as described herein, in an unfastened, unfolded and laid flat condition, and showing the surface of the training pants that faces away from the wearer.
Figure 2:
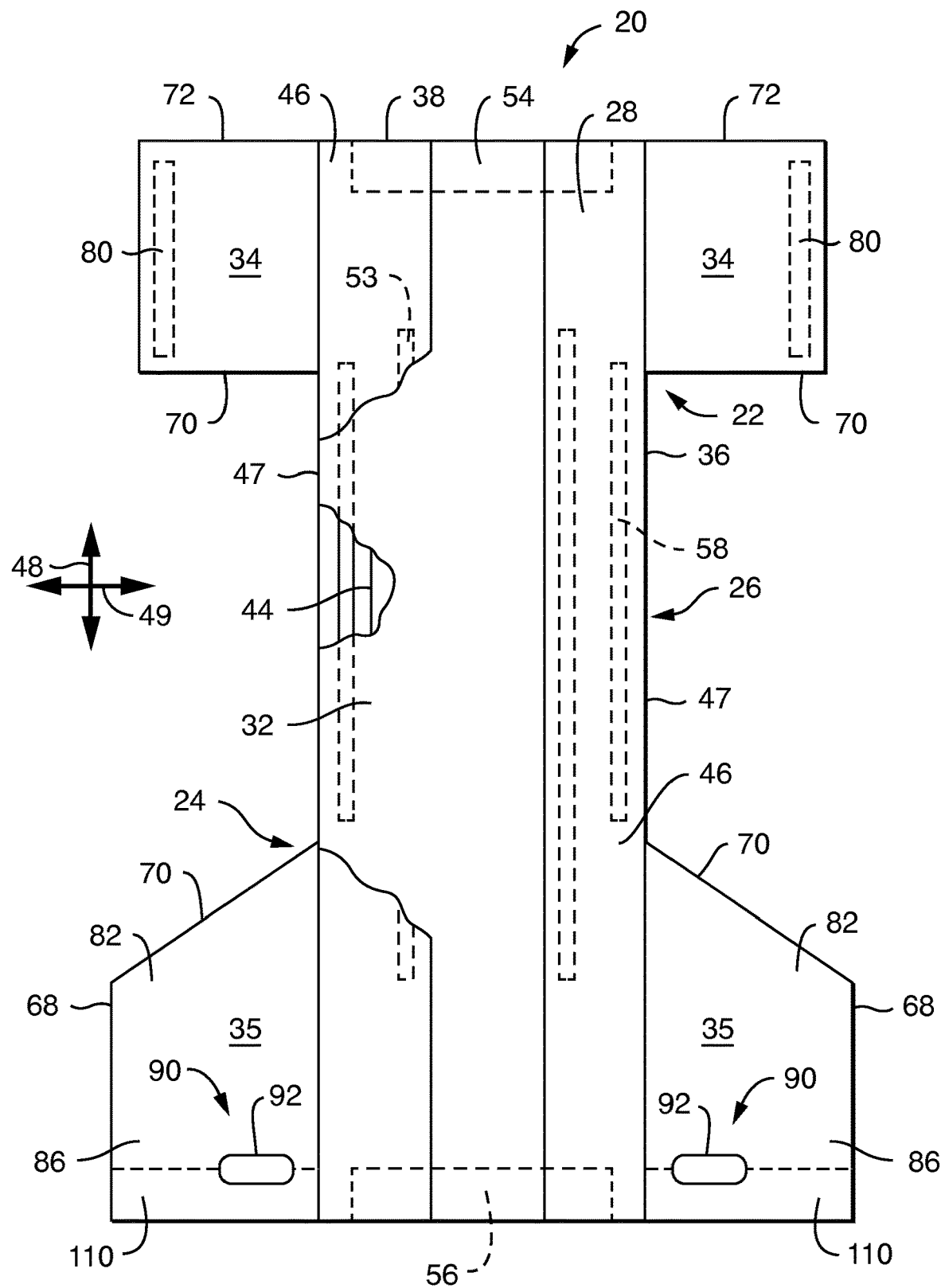
FIG. 2 is a top plan view of the product of FIG. 1 showing the surface of the training pants that faces the wearer when worn and with portions cut away to show underlying features.

"Cross direction assembly" refers to a process in which disposable absorbent products are manufactured in an orientation in which the products are connected side-to-side, in the transverse direction shown by arrow 49 in FIGS. 1 and 2, a process utilizing a cross direction assembly that entails products traveling through a converting machine parallel to the direction of arrow 49, as opposed to "machine direction assembly" in which the products are connected end-to-end or waist-to-waist.

"Disposable" refers to articles that are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite that can be elongated by at least 25 percent of its relaxed length and that will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to any woven, knitted and nonwoven fibrous webs.

"Film" refers to a thermoplastic film made using a film extrusion and/or forming process, such as a cast film or blown film extrusion process. The term includes apertured films, slit films, and other porous films that constitute liquid transfer films, as well as films that do not transfer liquid.

"Flexible" refers to materials that are compliant and that will readily conform to the general shape and contours of the wearer's body.

"Hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, while fibers having contact angles greater than 90 degrees are designated "nonwettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, can spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

"Longitudinal" and "transverse" have their customary meaning, as indicated by the longitudinal and transverse axes depicted in FIGS. 1 and 2. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Machine direction" refers to the length of a fabric in the direction in which it is produced, as opposed to "cross direction" that refers to the width of a fabric in a direction generally perpendicular to the machine direction.

"Machine direction assembly" refers to a process in which disposable absorbent products are manufactured in an orientation in which the products are connected end-to-end or waist-to-waist, in the longitudinal direction shown by arrow 48 in FIGS. 1 and 2, a process utilizing a machine direction assembly entails products traveling through a converting machine parallel to the direction of arrow 48, as opposed to "cross direction assembly" in which the products are connected side-to-side.

"Meltblown fiber" means fibers formed by extruding a molten thermoplastic material through a plurality of fine, usually circular, die capillaries as molten threads or filaments into converging high velocity heated gas (e.g., air) streams that attenuate the filaments of molten thermoplastic material to reduce their diameter, which can be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers that can be continuous or discontinuous, are generally smaller than about 0.6 denier, and are generally self bonding when deposited onto a collecting surface. Meltblown fibers used in the present disclosure are preferably substantially continuous in length.

"Member" when used in the singular can have the dual meaning of a single element or a plurality of elements.

"Nonwoven" and "nonwoven web" refer to materials and webs of material that are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged," and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment. It should be noted that a releasably attached or releasably engaged seam is a refastenable seam that does not include a bonded seam that must be torn, cut, or otherwise disrupted.

"Spunbonded fiber" refers to small diameter fibers that are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and that substantially returns to a nonsoftened condition when cooled to room temperature.

These terms can be defined with additional language in the remaining portions of the specification.

DETAILED DESCRIPTION

The present disclosure is directed to an absorbent article, and more specifically a personal wear absorbent article and still more specifically a pant-like absorbent garment having one or more handles disposed on a garment side panel for ease of removal and donning. To facilitate donning he handle is designed with strength sufficient to allow a user of the product to pull on the garment without tearing the product. Further when a toddler or caregiver grasps the handle to pull-on the product the handle is displaced, but does not break.

Referring now to the drawings and in particular to FIGS. 1 and 2, a personal wear absorbent article according to one aspect is illustrated in the form of a pants-type article for wear about a wearer's waist, and more particularly in the form of children's toilet training pants, indicated in its entirety by the reference numeral 20. The term absorbent generally refers to articles that can be placed against or in proximity to the body of the wearer to absorb and/or retain various liquid wastes discharged from the body. The absorbent article can be disposable, which refers to articles that are intended to be discarded after a limited period of use instead of being laundered or otherwise restored for reuse. It is understood that the concepts described herein are suitable for use with various other pants-type articles such as adult incontinence articles, as well as other articles intended for personal wear such as clothing, diapers, feminine hygiene products, medical garments, surgical pads and bandages, other personal care or health care garments, and the like without departing from the scope of the present disclosure.

By way of illustration only, various materials and methods for constructing the training pants 20 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference, in a manner consistent with the present disclosure.

Figure 3:
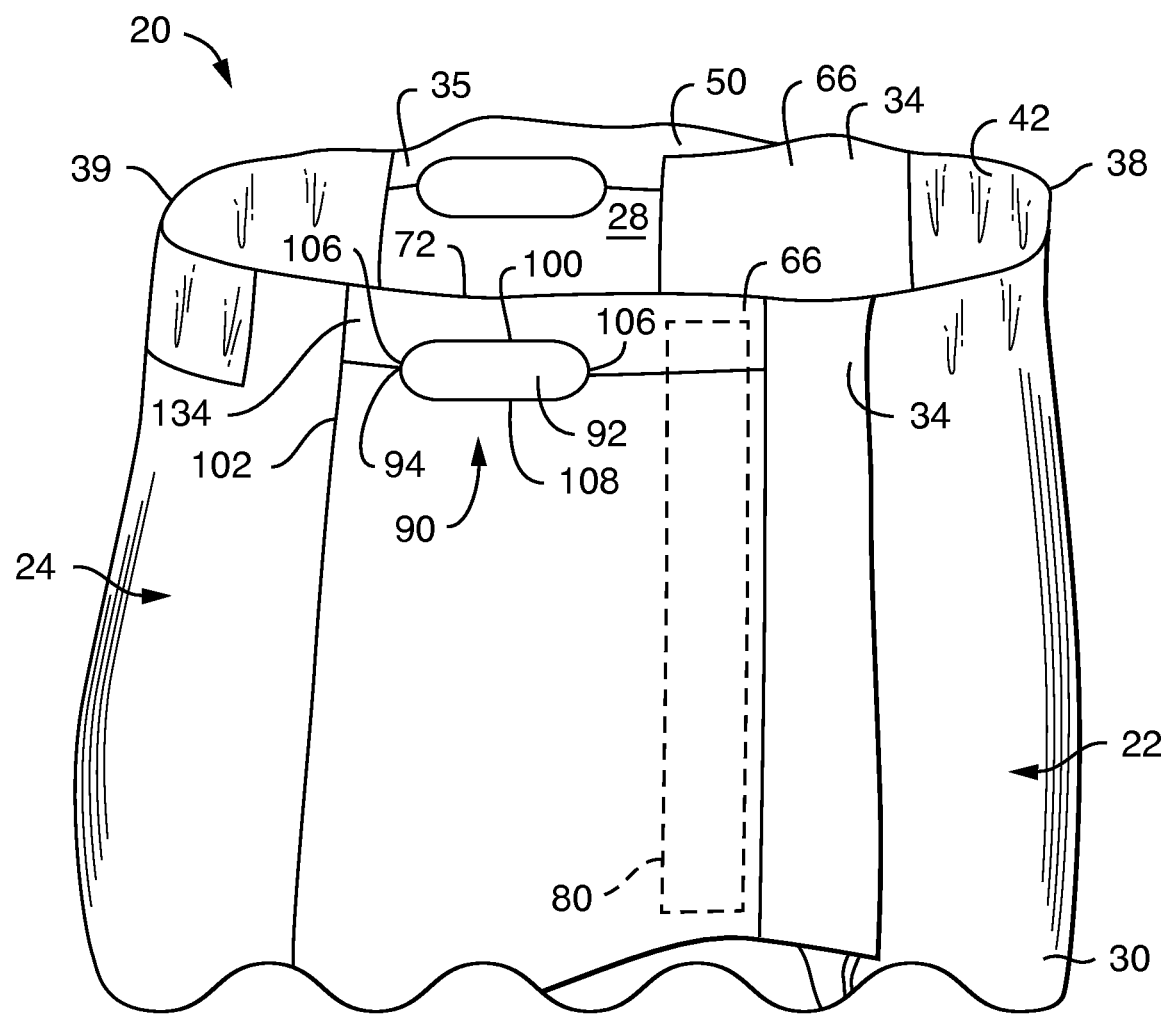
FIG. 3 is a partial schematic view illustrating the handle on the training pant illustrated in FIGS. 1-2.

The pair of training pants 20 is illustrated in FIG. 3 in a fully pre-assembled (i.e., as assembled during initial manufacture) configuration (broadly referred to herein as a wear configuration of the pants, i.e., absorbent article). With additional reference to FIGS. 1 and 2, the training pants 20 includes a front waist region 22, a back waist region 24, a crotch region 26 extending longitudinally between and interconnecting the front and back waist regions 22, 24 along a longitudinal direction of the pants, an inner surface 28 configured for contiguous relationship with the wearer, and an outer surface 30 opposite the inner surface 28. The training pants 20 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

The illustrated pants 20 includes a central absorbent assembly, generally indicated at 32, which when laid flat as in FIGS. 1 and 2 can be rectangular or any other desired shape. A pair of laterally opposite front side panels 34 extends outward from the absorbent assembly 32 at the front waist region 22 (thereby forming transversely outer portions of the front waist region 22, and more broadly in part forming transversely opposite sides of the training pants). Laterally opposite back side panels 35 extend outward from the absorbent assembly 32 at the back waist region 24 (thereby forming transversely outer portions of the back waist region 24, and together with the front side panels 34 further defining the sides of the pants).

The central absorbent assembly 32 of the illustrated aspect includes an outer cover 40 and a bodyside liner 42 (FIG. 3) connected to the outer cover 40 in a superposed relation by suitable means such as adhesives, ultrasonic bonds, thermal bonds or other conventional techniques. An absorbent structure 44 (FIG. 2) is disposed between the outer cover 40 and the bodyside liner 42. A pair of containment flaps 46 (FIG. 2) is secured to the bodyside liner 42 for inhibiting the lateral flow of body exudates. The central absorbent assembly 32 has opposite ends that form portions of the front and back waist edges 38 and 39, and opposite side edges 47 that form portions of the side edges 36 of the training pants 20 (FIGS. 1 and 2).

The absorbent assembly 32 and side panels 34, 35 can include two or more separate elements, as shown in FIGS. 1 and 2, or they can be integrally formed. Integrally formed side panels 34, 35 and absorbent assembly 32 would include at least some common materials, such as the bodyside liner 42, flap composite, outer cover 40, other materials and/or combinations thereof, and could define a one-piece elastic, stretchable, or nonstretchable pants 20. For further reference, arrows 48 and 49 in FIGS. 1 and 2 depict the orientation of a longitudinal axis and a transverse or lateral axis, respectively, of the training pants 20.

The front waist region 22 of the training pant 20 can be selectively joined to the back waist region 24 via a pair of refastenable side seams 66 (one side seam being shown in a fastened configuration and the other side seam being shown in an unfastened configuration) via an article fastening system 80 to define a pull-on, pant-like configuration of the training pant having a waist opening, indicated at 50, and two leg openings. The article fastening system 80 may include any suitable complementary refastenable fasteners including, for example and without limitation, hook- and loop-type fasteners, other types of mechanical fasteners, adhesive fasteners, cohesive fasteners, and combinations thereof. In some suitable embodiments, the fastening components 90, 92 may be pre-fastened during the manufacturing process of the training pant 20 such that the training pant 20 is supplied to the user in a fastened configuration. While FIG. 1 illustrates the front and back regions 22, 24 being joined together via refastenable seams 66, it is understood that the front and back regions can be joined together via non-refastenable, bonded seams (e.g., by adhesive bonding, ultrasonic bonding, pressure bonding, thermal bonding).

With the training pants 20 in the fastened condition as illustrated in FIG. 3, the front and back side panels 34, 35 are attached to each other by a primary, or article fastening system 80 to define the pre-assembled three-dimensional wear configuration of the pants 20, having a waist opening 50 and a pair of leg openings. The front waist region 22 includes the portion of the training pants 20 that, when worn, is positioned at least in part on the front of the wearer while the back waist region 24 includes the portion of the training pants 20 that is positioned at least in part on the back of the wearer. The crotch region 26 of the training pants 20 includes the portion of the training pants 20 that is positioned between the legs of the wearer and covers the lower torso of the wearer.

The front and back side panels 34 and 35 include the portions of the training pants 20 (and more particularly of the front and back waist regions 22, 24) that, when worn, are positioned on the hips of the wearer. The attached side panels 34, 35 thus broadly define the transversely opposite sides of the pants 20 at a refastenable seam 66 along which the fastening system 80 releasably attaches the front and back side panels 34, 35. The waist edges 38 and 39 of the training pants 20 are configured to encircle the waist of the wearer and together define the waist opening 50 (FIG. 3). Portions of the side edges 36 in the crotch region 26 generally define leg openings. The side panels 34 and 35 desirably have a panel length dimension measured parallel to the longitudinal axis 48 along the outer edge 68. Optionally, the panel length dimension of the back side panel 35 is longer than the front side panel 34.

The central absorbent assembly 32 is configured to contain and/or absorb exudates discharged from the wearer. For example, the containment flaps 46 are configured to provide a barrier to the transverse flow of body exudates. A flap elastic member 53 (FIG. 2) can be operatively joined with each containment flap 46 in any suitable manner as is well known in the art. The elasticized containment flaps 46 define a partially unattached edge that assumes an upright configuration in at least the crotch region 26 of the training pants 20 to form a seal against the wearer's body. The containment flaps 46 can be located along the side edges 36 of the pants 20, and can extend longitudinally along the entire length of the absorbent assembly 32 or can only extend partially along the length of the absorbent assembly 32. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 also suitably includes a front waist elastic member 54 (FIG. 2), a rear waist elastic member 56, and leg elastic members 58, as are known to those skilled in the art. The waist elastic members 54 and 56 can be attached to the outer cover 40 and/or the bodyside liner 42 along the opposite waist edges 38 and 39, and can extend over part or all of the waist edges. The leg elastic members 58 can be attached to the outer cover 40 and/or the bodyside liner 42 along the opposite side edges 36 and positioned in the crotch region 26 of the training pants 20. The leg elastic members 58 can be longitudinally aligned along each side edge 47 of the absorbent assembly 32.

The outer cover 40 suitably includes a material that is substantially liquid impermeable. The outer cover 40 can be a single layer of liquid impermeable material, but more suitably includes a multi-layered laminate structure in which at least one of the layers is liquid impermeable. The inner layer of the outer cover 40 can be both liquid and vapor impermeable, or it can be liquid impermeable and vapor permeable.

It is also contemplated that the outer cover 40 can be stretchable, and more suitably elastic. In particular, the outer cover 40 is suitably stretchable and more suitably elastic in at least the transverse or circumferential direction of the pants 20. In other aspects the outer cover 40 can be stretchable, and more suitably elastic, in both the transverse and the longitudinal direction.

The liquid permeable bodyside liner 42 is illustrated as overlying the outer cover 40 and absorbent structure 44, and can, but need not, have the same dimensions as the outer cover 40. The bodyside liner 42 is suitably compliant, soft feeling, and non-irritating to the child's skin. Further, the bodyside liner 42 can be less hydrophilic than the absorbent structure 44 to present a relatively dry surface to the wearer and permit liquid to readily penetrate through its thickness.

Alternatively, the bodyside liner 42 can be more hydrophilic or can have essentially the same affinity for moisture as the absorbent structure 44 to present a relatively wet surface to the wearer to increase the sensation of being wet. This wet sensation can be useful as a training aid. The hydrophilic/hydrophobic properties can be varied across the length, width and/or depth of the bodyside liner 42 and absorbent structure 44 to achieve the desired wetness sensation or leakage performance.

The bodyside liner 42 can also be stretchable, and more suitably elastic. In particular, the bodyside liner 42 is suitably stretchable and more suitably elastic in at least the transverse 49, or circumferential direction of the pants 20. In other aspects, the bodyside liner 42 can be stretchable, and more suitably elastic, in both the transverse 49 and the longitudinal 48 directions.

As noted previously, the illustrated training pants 20 have front and back side panels 34 and 35 defining transversely opposite sides of the pants 20 in the wear configuration of the pants 20. The side panels 34, 35 can be permanently attached along seams 66 to the central absorbent assembly 32 in the respective front and back waist regions 22 and 24. More particularly, as seen best in FIG. 1, the front side panels 34 can be permanently attached to and extend transversely outward beyond the side edges 47 of the absorbent assembly 32 in the front waist region 22, and the back side panels 35 can be permanently attached to and extend transversely outward beyond the side edges 47 of the absorbent assembly 32 in the back waist region 24. The side panels 34 and 35 can be attached to the absorbent assembly 32 using attachment means known to those skilled in the art such as adhesive, thermal, pressure or ultrasonic bonding. Alternatively, the side panels 34 and 35 can be formed as an integral portion of a component of the absorbent assembly 32. For example, the side panels 34, 35 can include a generally wider portion of the outer cover 40, the bodyside liner 42, and/or another component of the absorbent assembly 32.

The front and back side panels 34, 35 each have an outer edge 68 spaced laterally from the seam 66, a leg end edge 70 disposed toward the longitudinal center of the training pants 20, and a waist end edge 72 disposed toward a longitudinal end of the training pants 20. The leg end edge 70 and waist end edge 72 extend from the side edges 47 of the absorbent assembly 32 to the outer edges 68. The leg end edges 70 of the side panels 34 and 35 form part of the side edges 36 of the training pants 20. The leg end edges 70 of the illustrated aspect are suitably curved and/or angled relative to the transverse axis 49 to provide a better fit around the wearer's legs. However, it is understood that only one of the leg end edges 70 can be curved or angled, such as the leg end edge 70 of the back waist region 24, or neither of the leg end edges 70 can be curved or angled, without departing from the scope of this disclosure. The waist end edges 72 are suitably parallel to the transverse axis 49. The waist end edges 72 of the front side panels 34 form part of the front waist edge 38 of the training pants 20, and the waist end edges 72 of the back side panels 35 form part of the back waist edge 39 of the pants 20.

The side panels 34, 35 suitably, although not necessarily, include a stretchable material capable of stretching in a direction generally parallel to the transverse axis 49 of the training pants 20. More suitably the side panels 34, 35 include an elastic material. Suitable elastic materials, as well as one process of incorporating stretchable side panels into training pants, are described in the following U.S. Pat. Nos.: 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sept. 10, 1991 to Vogt et al.; all of which are incorporated herein by reference. Optionally, the stretch material can include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and PCT application WO 01/88245 in the name of Welch et al.; all of which are incorporated herein by reference. Other suitable materials are described in U.S. patent application Ser. No. 12/649,508 to Welch et al. and U.S. Pat. No. 8,287,677 to Lake et al., all of which are incorporated herein by reference.

Alternatively, the side panel material can include other woven or nonwoven materials, such as those described above as being suitable for the outer cover 40 or bodyside liner 42; mechanically pre-strained composites; or stretchable but inelastic materials.

Figure 4A:
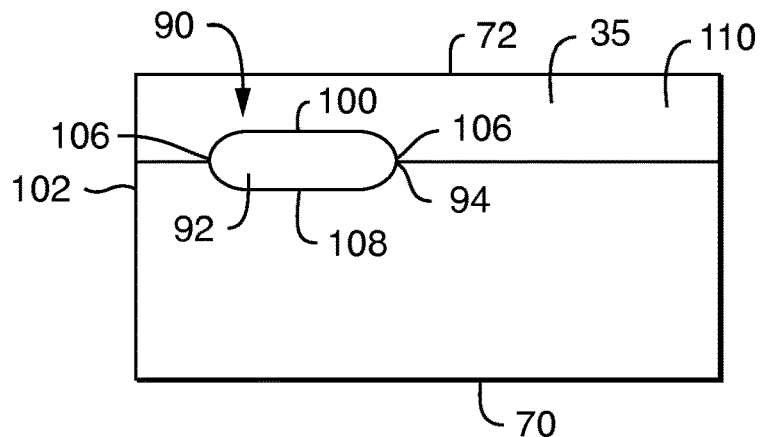
FIGS. 4a-4e is a partial view of different embodiments of the handle shape and size on a side panel; and Repeat use of reference characters in the present specification and drawings is intended to represent the same or analogous features or elements of the present disclosure. The drawings are representational and are not necessarily drawn to scale. Certain proportions thereof might be exaggerated, while others might be minimized.
Figure 4B:
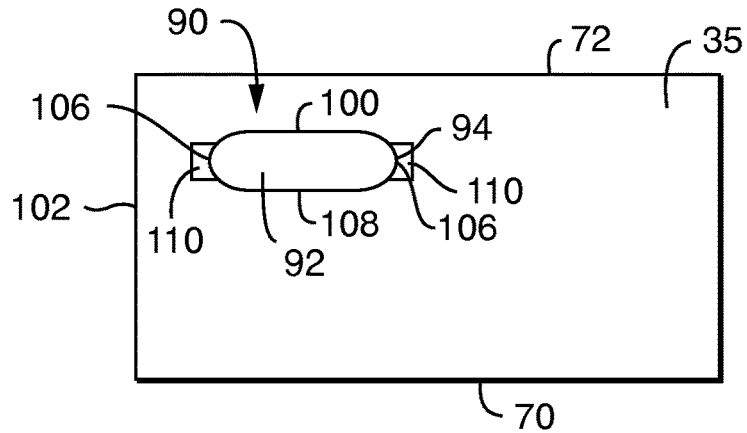
Figure 4C:
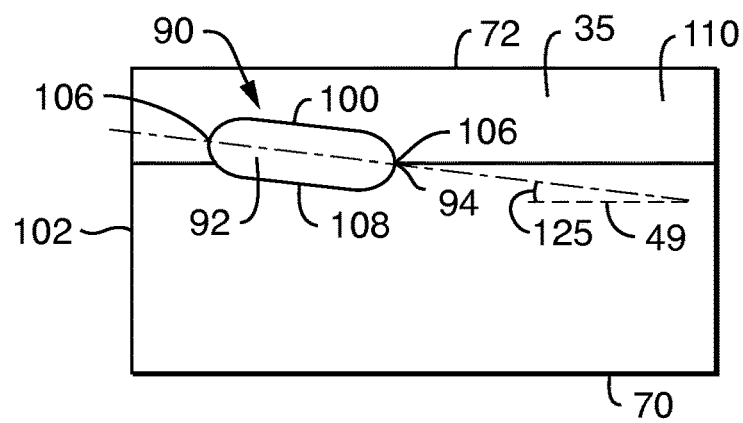
Figure 4D:
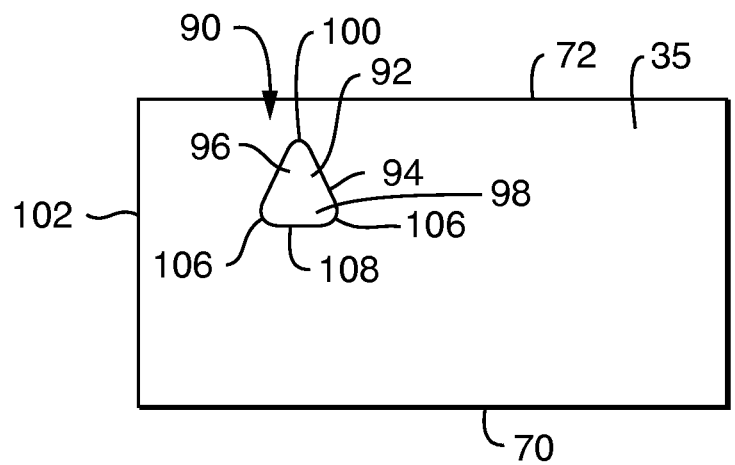

A handle 90 is formed in at least one side panel of the training pants 20. The handle 90 is formed by cutting an aperture 92 having a longitudinal midpoint 94, a top portion 96 and a bottom portion 98 through the side panel material 35 as illustrated in FIG. 4d. The handle 90 must have sufficient strength to enable the user to pull on the training pants 20 without causing too much displacement in the material. If the handle 90 is too weak, the material will stretch too far causing the article to be stuck around the knees or buttocks while being pulled on or not being placed in the correct position such that it is snug against the wearer's body and is improperly positioned to accept waste.

The size and location of the handle 90 may also increase the functionality of the handle as it is optimized to enable independence for a toddler who is learning potty training. For example, the width of the aperture 92, measured as the greatest distance as measured in a laid-flat, relaxed condition in the transverse direction 49 prior to use of the product may enable a user, typically a toddler child, the ability to place their fingers and hands through the aperture and pull on the product. However, the width of the aperture 92 should not be so great so as to allow for too much displacement during donning and cause issues with the article's effectiveness. Further, in certain instances a user may use less than four fingers to grasp the handle 90, such as only one or two fingers. As a result, an optimal width for the aperture 92 may be from about 20 mm and about 50 mm, such as from about 25 to about 40 mm and more desirably about 30 mm.

The location of the handle 90 can also be important to its ability to function correctly. Similarly, when handle is disposed longitudinally 49 proximal to the leg edge 70 the handle 90 is difficult for a user to grasp or the pant 20 becomes difficult to guide onto the body. As a result, distance between the handle 90 and the waist edge 70 may be optimized. For example, the handle 90 comprising an aperture 90 with a top edge 100 may disposed on the side panel 35 such that there is between about 10 and about 35 mm, such as from about 15 to about 25 and more desirably about 20 mm, from the top edge 100 to the waist edge 70 of the side panel 35, as measured when the handle is non-extended.

Location of the handle 90 laterally 49 on the side panel 35 may also be considered to improve the handle effectiveness. It has been found that a handle 90 laterally 49 close to the refastenable seam 66 causes excessive displacement or tearing, and laterally 49 close to the effective edge 102 of the side panel 35 is difficult to grab or guide the article on the body. As a result, the handle 90 comprising a back distal edge may be disposed on the side panel 35 such that the distance between the back distal edge and the effective edge 102 of the side panel is from about 10 mm and about 35 mm, such as from about 15 to about 25 mm and more desirably about 20 mm, as measured when the handle is non-extended. For purposes herein and illustrated in FIG. 3, an effective edge 102 of the side panel 35 is the location where the side panel 35 is bonded to the absorbent assembly 32. In cases, where the side panel is integral with the absorbent assembly 32, the effective edge is where the absorbent core is attached to the outer cover 40.

The handle 90 may be formed on the side panel 35 at an angle 125 relative to lateral axis 49 of the side panel 35 to increase ease of use and strength. Angled handles can enable controlling and directing stress and strain resulting from donning. One potential benefit of controlling the force concentrations is to insure they do not occur adjacent to the distal ends of refastenable seams and potentially cause the seam to pop open during donning. As illustrated in FIG. 4c, the handle 90 may be placed on the side panel 35 at an angle 125 relative to the lateral axis 49 of the side panel 35 to increase ease of use and strength. Desirably, the handle 90 may be have an angle 125 of at least 2.5 degrees, and more desirably at an angle 125 of between about 10 and about 20 degrees relative to the transverse axis 49 of the side panel 35.

Figure 4E:
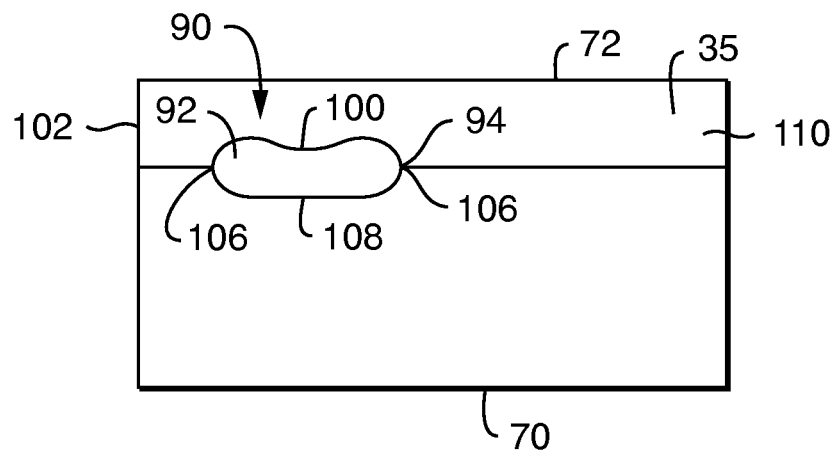

The aperture 92 may be any shape known to one skilled in the art including an oval, rectangle, triangle, bean or similar shapes. The shape may also correspond to other graphics on the training pants 20 to provide an overall training pants 20 theme. FIGS. 4a-4e illustrate various examples of the different shapes the handle could form that would allow for a functioning handle. In one particular embodiment illustrated in FIG. 4a-c, the aperture has a rectangular oval shape having a maximum width. In FIG. 4c, he aperture is placed at an angle relative to the waist edge. FIG. 4e illustrates an alternative shape for the aperture illustrating a bean-shaped aperture.

In FIG. 4d, the aperture 92 is formed having a top portion 96 and a bottom portion 98. The aperture 92 has a maximum width at the bottom portion 98 of the aperture 92 and the aperture 92 decreases in width from the bottom portion 98 to the top portion 96. Alternatively, the aperture 92 has a width at the bottom portion 98 of the aperture 92 and the aperture 92 increases in width from the bottom portion 98 to the top portion 96. Optionally, the aperture 92 includes a rounded corner at its top edge 104 as a rounded corner will provide less tearing of the training pants 20. Optionally, the aperture 92 may be a rounded triangle as illustrated in FIG. 4d. This shape helps provide the ability to manage greater maximum stress/strain without inhibiting stretch of the handle. This results in a good balance of displacement and strength, even without a reinforcing material.

To provide the necessary strength in the product for handle functionality, the handle 90 may include a reinforcing material 110 operatively joined adjacent and extending laterally from the distal side edges 106 of the aperture 92 as illustrated in the Figures. The reinforcing material 110 may be a separate piece or multiple pieces of material attached to the at least one side panel. Alternatively, the reinforcing material 110 may include a portion of the side panel folded over itself. In this embodiment, the reinforcing material may act also as a waistband for the article.

When the handle 90 is being used to pull-on the product, lateral and longitudinal forces are placed on the handle 90. Operatively joining the reinforcing material 110 at the longitudinal midpoint 94 of the distal side edges 106 of the aperture 92 helps provide the ability to manage greater maximum stress/strain without inhibiting stretch of the handle 90. This provides good balance of displacement and strength. One potential benefit of controlling the force concentrations is to insure they do not occur adjacent to the distal ends of refastenable seams and potentially cause the seam to pop open during donning. In one embodiment, as illustrated in 4b, the reinforcing material 110 comprises a material extending longitudinally from at least a midpoint between the longitudinal midpoint 94 of the aperture 92 and a top edge 100 of the aperture 92 to at least a midpoint between the longitudinal midpoint 94 of the aperture 92 and a bottom edge 108 of the aperture 92. In another embodiment, as illustrated in FIG. 4a, he reinforcing material 110 comprises a material extending longitudinally from a waist edge 72 to at least the longitudinal midpoint 94 of the aperture 92.

Alternatively, the reinforcing material 110 may extend from at least one tangent point defined by a tangent line in the longitudinal direction from the aperture 92. The tangent points are defined at the distal side edges 106 of the aperture 92 relative to the transverse axis 49. In other words, the tangent point may be defined by the closest and farthest points on aperture 92 to the effective edge of the side panel relative to the transverse axis 49 that would result in a longitudinal tangent line. Since the stresses on the handle may be greatest at these tangent points, extending the reinforcing material from the aperture 92 at this location may help to provide the ability to manage greater maximum stress/strain without inhibiting stretch of the handle 90. If the shape is not symmetrical, the tangent points on either side edge of the aperture 92 may not be at the same point on the longitudinal axis 48 of the article. This could result in a tangent point defined by a tangent line in the longitudinal direction on one side edge 106 closer to the waist edge 72 of the side panel 35 and a tangent point defined by a tangent line in the longitudinal direction on the other side edge 106 closer to the leg edge 70 of the side panel 35. In one embodiment, the reinforcing material 110 may extend from both side edges 106 of the aperture 92 at the tangent point that is closer longitudinally to the waist edge 72 of the side panel 35. More desirably, the reinforcing material may extend from both side edges of the aperture at the tangent point that is closer longitudinally to the leg edge of the side panel.

For example, as illustrated in 4e, the reinforcing material 110 comprises a material extending from at least the distal side edge 106 of the aperture 92 that exists at the tangent point on the longitudinal axis 48 closer to the leg edge 70 of the product. Alternatively, while not shown, the reinforcing material 110 in FIG. 4e may extend from at least the distal side edge 106 of the aperture 92 that exists at the tangent point on the longitudinal axis 48 closer to the waist edge 70 of the product. In another embodiment, as illustrated in FIG. 4a, the reinforcing material 110 comprises a material extending from at least the distal side edge 106 of the aperture 92 that exists at the tangent point on the longitudinal axis. In this embodiment with a symmetrical rectangular oval, the tangent points on both sides of the aperture 92 are at the same longitudinal location at the distal side edges 106.

The reinforcing material 110 may be the same material as the side panel 35 or different material than the side panel 35. The reinforcing material 110 may suitably, although not necessarily, include a stretchable material capable of stretching in a direction generally parallel to the transverse axis 49 of the training pants 20. More suitably the reinforcing material includes an elastic material. Suitable elastic materials are described in the following U.S. Pat. Nos.: 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. Optionally, the reinforcing material can include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Other suitable materials are described in U.S. patent application Ser. Nos. 12/649,508 to Welch et al. and U.S. Pat. No. 8,287,677 to Lake et al., all of which are incorporated herein by reference.

Alternatively, the reinforcing material 110 can include other woven or nonwoven materials, such as those described above as being suitable for the outer cover 40 or bodyside liner 42; mechanically pre-strained composites; or stretchable but inelastic materials.

Optionally, the reinforcing material 110 is a different color or pattern than the side panel 35 material. This is a visual cue directing the hand to the handle 90. In addition, the double thickness provided by the reinforcing material 110 on the side panel 35 provides tactile cues that help locate the proper hand position for grasping the handle 90. This may make the handle more intuitive for grasping by a toddler.

To illustrate the importance of the design of the handle 90, children having a weight between 18 and 34 pounds were each asked to put on and take off six training pants having handles to measure the number of tears.

Code 1 tested included a 2T/3T pant design with an SBL single side panel having 74 mm of functional stretch and a handle with its top edge placed 17.5 mm from the top edge of the side panel and its back edge placed 15 mm from the back functional edge of the side panel. Code 1 included an SBL reinforcement material extending to the waist edge of the side panel attached via adhesive and an aperture having a rectangular oval shape as illustrated in FIG. 4a having a width of 30 mm. Three other codes, Codes 2, 3, and 4 were tested included a 2T/3T pant design with an SBL single side panel having 81 mm of functional stretch and a handle with its top edge placed 27.5 mm from the top edge of the side panel and its back edge placed 15 mm from the back functional edge of the side panel. Code 2 included no reinforcing material and an aperture having a rectangular oval having a width of 30 mm. Code 3 included no reinforcing material and an aperture having a rectangular oval having a width of 30 mm at an angle of 15 degrees. Code 4 included no reinforcing material and an aperture having a rounded triangle shape as illustrated in FIG. 4c having a maximum width of 30 mm and a height of 30 mm.

TABLE 1

Handle Tears

| Code | 1 | 2 | 3 | 4 |
|---|---|---|---|---|
| Products with Some Tearing (%) | 2% | 43% | 50% | 5% |
| Products with Complete Tears (%) | 2% | 7% | 2% | 0% |

After the child was finished trying on the products, each product was inspected for tears at the handle. As illustrated in Table 1 above, the Code 4 rounded triangle shaped handle and the Code 1 reinforced rectangular oval shaped handle had a much lower tearing frequency versus the Code 2 non-reinforced rectangular oval shaped handle. The Code 3 angled handle had a much lower complete tearing frequency versus the Code 2 rectangular oval shaped handle.

Code 5 tested included a 2T/3T pant design with an SBL single side panel having 81 mm of functional stretch and a handle with its top edge placed 20 mm from the top edge of the side panel and its back edge placed 15 mm from the back functional edge of the side panel. Code 5 included an SBL reinforcement material extending to the waist edge of the side panel attached via adhesive and an aperture having a bean-shape as illustrated in FIG. 4c having a width of 30 mm. Three other codes, Codes 6, 7, and 8 were tested included a 2T/3T pant design with an SBL single side panel having 81 mm of functional stretch and a handle with its top edge placed 20 mm from the top edge of the side panel and its back edge placed 15 mm from the back functional edge of the side panel. Code 6 included a reinforcing material extending 50 mm and an aperture having a bean shape having a width of 30 mm. Code 7 included no reinforcing material and an aperture having a bean shape having a width of 30 mm. Code 8 included a reinforcing material extending 30 mm and an aperture having a rounded triangle shape as illustrated in FIG. 4c having a width of 30 mm. Code 9 included a reinforcing material extending 50 mm and an aperture having a rounded triangle shape having a maximum width of 30 mm and a height of 30 mm. Code 10 included no reinforcing material and an aperture having a rounded triangle shape having a width of 30 mm.

In addition, handle peak tensile strength and displacement at 600 grams-force to represent a toddler pulling-on the handle was also tested for the Codes described above. Handle peak tensile strength and displacement were calculated as described in the test method below. 3 samples were tested and averaged to develop the result.

TABLE 2

Handle strength and Displacement

| Code | 5 | 6 | 7 | 8 | 9 | 10 |
|---|---|---|---|---|---|---|
| Peak Tensile Strength (grams-force) | 3063 | 4791 | 2407 | 3372 | 4493 | 3151 |

TABLE 2-continued

Handle strength and Displacement

| Code | 5 | 6 | 7 | 8 | 9 | 10 |
|---|---|---|---|---|---|---|
| Displacement at 900 grams-force (mm) | 30.8 | 29.9 | 48.1 | 26.0 | 25.4 | 33.3 |

As illustrated in Table 2, the reinforced handles had a much higher strength than versus non-reinforced handles. In addition, all of the codes had similar ability to be displaced.

Desirably, the handle 90 may have a peak tensile strength of at least 2300 grams. Desirably, the handle 90 may have a peak tensile strength of between about 3000 grams and 7000 grams. More desirably, the handle 90 may have a peak tensile strength of between 4000 grams and 7000 grams. In addition, the handle 90 having a displacement of between 5 mm and 50 mm at a force of 900 grams-force. The nexus of these two features combined together allows for a handle 90 that helps provide the ability to manage greater maximum stress/strain without inhibiting stretch of the handle 90. Thus, the handle provides a good balance of displacement and strength to allow a toddler or other user to don or pull-on the product.

Peak Tensile and Displacement Test

The peak tensile load of the handle and displacement of the handle can be quantified using the following Peak Tensile and Displacement Test method, which is designed to quantify, in grams, the peak tensile load and the displacement of the material in the handle of the absorbent article. The displacement of the handle is that direction in which the side panel material would generally be displaced as a user pulls-on a substrate when the product is in use.

Equipment

1. Constant rate of extension tensile tester equipped with an appropriate load cell. A suitable tensile testing system is a Sintech Tensile Tester, commercially available from MTS, Research Triangle Park, N.C., under the trade designation Sintech Model 1/G Tensile Tester.

2. Software commercially obtained from MTS under the trade designation MTS TESTWORKS® for Windows Version 4.12.

3. Pneumatic-action grips commercially available from Instron Corporation, Canton, Mass., under the trade designation Instron Model 2712-004.

4. 2.5 cm. by 10.1 cm. (1 by 4 inch) grip faces, serrated, commercially available from Instron Corporation, Canton, Mass.

4. 10 mm diameter metal rod.

5. Test facility having a temperature of 23±1° C., and a relative humidity of 50±2 percent.

Test Procedure

1. A sample to be tested is conditioned in the test facility for at least 4 hours prior to testing.

3. The load cell is calibrated and the software loaded.

4. The grips are installed on the tensile tester with the jaws closed.

5. The test conditions for the tensile tester are set as follows:
Crosshead speed: 305 millimeters/minute
Full-scale load: 10 kilograms (22 lbs.)
Gage length: 50.8 millimeters (2 inches) (Measured from the crook of the hook fixture to the top of the grip face of the bottom fixture.)

6. The weight of the clamp is tared out.

7. The leg edge of the side panel of the article is inserted into the lower jaw directly below the handle.

8. The metal rod is inserted into the handle, such that the top edge of the handle rests on the crook of the metal rod. The lower jaw is closed, making sure the load is less than 10 grams.

9. The crosshead is started in motion, and the test is run until the handle breaks.

10. The peak tensile load needed to break the handle and the displacement of the material grams is recorded for the handle. The displacement is collected at 600 grams-force.

When introducing elements of the present disclosure or the preferred aspect(s) thereof, the articles "a," "an," and "the" are intended to mean that there are one or more of the elements. The terms "comprising," "including," and "having" are intended to be inclusive and mean that there can be additional elements other than the listed elements.

The disclosure has been described with reference to various specific and illustrative aspects and techniques. However, it should be understood that many variations and modifications can be made while remaining within the spirit and scope of the disclosure. Many alternatives, modifications and variations will be apparent to those skilled in the art in light of the foregoing description. Accordingly, this disclosure is intended to embrace all such alternatives, modifications, and variations that fall within the spirit and scope of the appended claims.

We claim:

1. An absorbent article for personal wear about a wearers waist, the article having a transverse axis and a longitudinal centerline, the article comprising:
an absorbent assembly having a front waist region, a back waist region, and a crotch region extending longitudinally between and interconnecting the front and back waist regions, the absorbent assembly comprising:
a liquid permeable bodyside liner facing the wearer;
an outer cover facing away from the wearer;
an absorbent body disposed therebetween;
interconnecting the front and back waist regions;
a front elastomeric side panel attached to the front waist region of the absorbent assembly and extending outward from the absorbent assembly and a back elastomeric side panel attached to the back waist region of the absorbent assembly and extending outward from the absorbent assembly, the front elastomeric side panel and the back elastomeric side panel refastenably coupled together along a refastenable side seam and defining at least a portion of a waist opening and a leg opening spaced from the waist opening when the article is in a wear configuration, wherein each of the front elastomeric side panel and the back elastomeric side panel extends from the waist opening to the leg opening; and
at least one handle comprising an aperture formed through only one of the front elastomeric side panel and the back elastomeric side panel, the aperture having a longitudinal midpoint, the handle further comprising a reinforcing material adjacent distal side edges of the aperture, the reinforcing material operatively joined to the elastomeric side panel comprising the aperture.

2. The article of claim 1 wherein the reinforcing material extends from the longitudinal midpoint of the aperture.

3. The article of claim 1 wherein the reinforcing material comprises a material extending longitudinally from a waist edge to at least a midpoint between the longitudinal midpoint of the aperture and a bottom edge of the aperture.

4. The article of claim 1 wherein the reinforcing material comprises a material extending longitudinally from at least a midpoint between the longitudinal midpoint of the aperture and a top edge of the aperture to at least a midpoint between the longitudinal midpoint of the aperture and a bottom edge of the aperture.

5. The article of claim 1 wherein the reinforcing material comprises a material extending from a waistband to at least the longitudinal midpoint of the aperture.

6. The article of claim 1 wherein the back elastomeric side panel is wider than the front side panel.

7. The article of claim 1 wherein the elastomeric side panel comprising the aperture is formed of a plurality of layers of material and wherein the reinforcing material comprises the same plurality of layers of material as the elastomeric side panel comprising the aperture.

8. The article of claim 1 wherein the reinforcing material comprises a different material than the elastomeric side panel comprising the aperture.

9. The article of claim 1 wherein the reinforcing material extends out from the distal side edge of the aperture.

10. The article of claim 1 further comprising the handle having a displacement in the longitudinal direction of between 5 mm and 50 mm at a force of 600 grams-force.

11. The article of claim 1 wherein the handle comprises a peak tensile strength between 3000 grams-force and 7000 grams-force in the longitudinal direction.

12. The article of claim 1 wherein the handle comprises a peak tensile strength of at least 2300 grams-force in the longitudinal direction.

13. The article of claim 1, wherein the reinforcing material comprises a material extending longitudinally from a waist edge to at least 50% between the longitudinal midpoint of the aperture and a bottom edge of the aperture.

14. The article of claim 2, wherein the reinforcing material comprises a material extending longitudinally from at least 50% between the longitudinal midpoint of the aperture and a top edge of the aperture to at least 50% between the longitudinal midpoint of the aperture and a bottom edge of the aperture.

15. The article of 1 wherein the back elastomeric side panel is longer than the front elastomeric side panel.

16. The article of claim 1 wherein the reinforcing material is selected from a separate piece of continuous material, multiple pieces of material adjacent the distal side edges of the aperture, and a folded waistband material.

17. The article of claim 1 wherein the handle is at an angle of at least 2.5 degrees relative to the transverse axis of the elastomeric side panel comprising the aperture.

18. The article of claim 1 wherein the handle is at an angle of between about 10 and about 20 degrees relative to the transverse axis of the elastomeric side panel comprising the aperture.

19. The absorbent article of claim 1, wherein the handle comprising the aperture is formed through the back elastomeric side panel.

20. The article of claim 1, wherein the aperture has a tangent point defined by a tangent line in the longitudinal direction at a side edge of the aperture.

21. The article of claim 20 wherein the aperture has a back tangent point defined by a tangent line in the longitudinal direction closer in the transverse direction to the back waist region and a front tangent point defined by a tangent line in the longitudinal direction closer in the transverse direction to the front waist region.

22. The article of claim 21 wherein one of the back tangent point and a front tangent point is closer longitudinally to the waist edge of the elastomeric side panel comprising the aperture, the reinforcing material extending from both side of the aperture at the one of the back tangent point and the front tangent point that is closer longitudinally to the waist edge of the elastomeric side panel comprising the aperture.

23. The article of claim 21 wherein one of the back tangent point and a front tangent point is closer longitudinally to the leg edge of the elastomeric side panel comprising the aperture, the reinforcing material extending from both side edges of the aperture at the one of the back tangent point and the front tangent point that is closer longitudinally to the leg edge of the elastomeric side panel comprising the aperture.

24. The article of claim 1, wherein the aperture has a maximum width of between about 20 mm and about 50 mm, and wherein a top edge of the aperture is located between about 10 and about 35 mm from the waist edge.

25. The article of claim 24 wherein the maximum width of the handle is about 30 mm.

26. The article of claim 1 wherein a back distal side edge of the aperture is located between about 10 and about 35 mm from an effective edge of the elastomeric side panel comprising the aperture.

27. The article of claim 1, wherein the elastomeric side panel comprising the aperture comprises a laminate material forming a first laminate material layer.

28. The article of claim 1, wherein the reinforcing material comprises a stretchable material.

29. The article of claim 27, wherein the reinforcing material comprises the laminate material of the elastomeric side panel comprising the aperture and forms a second laminate material layer.

30. The article of claim 1, wherein the aperture is disposed closer to the back waist region of the absorbent assembly than the refastenable side seam.

31. The article of claim 1, wherein the reinforcing material comprises a portion of the elastomeric side panel comprising the aperture folded over itself.

* * * * *